US009227912B2

(12) United States Patent
Marvin et al.

(10) Patent No.: US 9,227,912 B2
(45) Date of Patent: Jan. 5, 2016

(54) PROCESS FOR MAKING ETHANOLAMINES

(71) Applicant: Scientific Design Company, Inc., Little Ferry, NJ (US)

(72) Inventors: Katelyn Marvin, Maplewood, NJ (US); Barry Jay Billig, Irvington, NY (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 14/578,784

(22) Filed: Dec. 22, 2014

(65) Prior Publication Data

US 2015/0183719 A1 Jul. 2, 2015

Related U.S. Application Data

(60) Provisional application No. 61/921,810, filed on Dec. 30, 2013.

(51) Int. Cl.
*C07C 213/04* (2006.01)
*C07C 213/10* (2006.01)

(52) U.S. Cl.
CPC ............ *C07C 213/10* (2013.01); *C07C 213/04* (2013.01)

(58) Field of Classification Search
CPC ..................................................... C07C 213/04
See application file for complete search history.

(56) References Cited

U.S. PATENT DOCUMENTS

| 2,196,554 | A | 4/1940 | Guinot |
| 3,563,914 | A | 2/1971 | Wattimena |
| 3,702,259 | A | 11/1972 | Nielsen |
| 3,962,285 | A | 6/1976 | Cusumano |
| 4,119,670 | A * | 10/1978 | Tsuchiya ..................... 564/477 |
| 4,169,856 | A | 10/1979 | Cocuzza et al. |
| 4,335,181 | A | 6/1982 | Marano, Jr. et al. |
| 4,355,181 | A | 10/1982 | Willis, Jr. et al. |
| 4,761,394 | A | 8/1988 | Lauritzen |
| 4,766,105 | A | 8/1988 | Lauritzen |
| 4,845,296 | A | 7/1989 | Ahmed et al. |
| 4,908,343 | A | 3/1990 | Bhasin |
| 5,011,807 | A | 4/1991 | Hayden et al. |
| 5,057,481 | A | 10/1991 | Bhasin |
| 5,099,041 | A | 3/1992 | Hayden et al. |
| 5,102,848 | A | 4/1992 | Soo et al. |
| 5,187,140 | A | 2/1993 | Thorsteinson et al. |
| 5,407,888 | A | 4/1995 | Herzog et al. |
| 2002/0123653 | A1 * | 9/2002 | Tsuneki et al. ............... 564/475 |
| 2007/0037991 | A1 | 2/2007 | Rizkalla |
| 2010/0087684 | A1 | 4/2010 | Do et al. |

FOREIGN PATENT DOCUMENTS

| EP | 2 177 501 A1 | 4/2010 |
| GB | 760215 | 10/1956 |
| GB | 1529193 | 10/1978 |

OTHER PUBLICATIONS

Jisuanji Yu Yingyong Huaxue, 2011, 28(12), 1505-1508.*
International Search Report and Written Opinion dated Mar. 18, 2015 received in corresponding foreign International Application No. PCT/US2014/071820.

* cited by examiner

*Primary Examiner* — Sudhakar Katakam
(74) *Attorney, Agent, or Firm* — Scully, Scott, Murphy & Presser, P.C.

(57) ABSTRACT

A process for the preparation of ethanolamines comprising reacting a water-ammonia solution with ethylene oxide to form an effluent reaction mixture comprising unreacted ammonia, water and ethanolamines. This effluent reaction mixture is then subjected to a succession of steps to, inter alia, separate the ethanolamines.

11 Claims, 1 Drawing Sheet

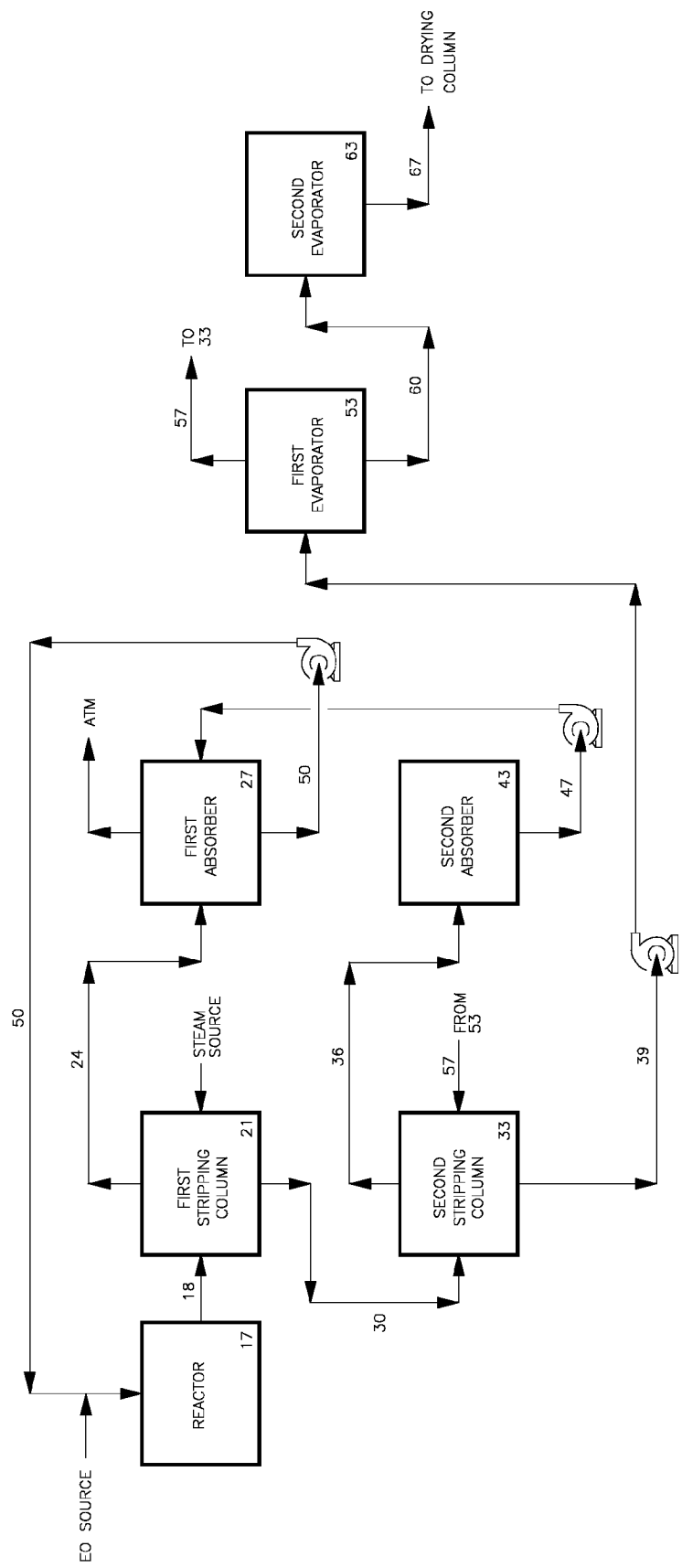

PROCESS FOR MAKING ETHANOLAMINES

CROSS REFERENCE TO RELATED APPLICATION

The present invention claims the benefit of U.S. Provisional Patent Application No. 61/921,810 filed Dec. 30, 2013, the entire content and disclosure of which is incorporated herein by reference.

FIELD OF THE INVENTION

The present invention relates to a method for the production of ethanolamines by reacting ammonia and ethylene oxide.

BACKGROUND OF THE INVENTION

Ethanolamines were first synthesized in a laboratory setting in 1860 when the pioneering Alsatian chemist Charles-Adolphe Wurtz heated ethylene chlorohydrin with aqueous ammonia in a closed tube. While never commercially interesting during the nineteenth century, ethanolamines were nonetheless enough of a technical curiosity that they attracted considerable technical interest. For example, the great German chemist Ludwig Knorr significantly improved upon Wurtz's work when in 1897 he successfully separated ethanolamines into their mono-, di- and triethanolamine component parts, as well as made other contributions to their synthesis.

Despite process improvements and continued laboratory interest, ethanolamines only attracted substantial commercial development after 1945. At this time, the significant increase in the industrial production of ethylene oxide was also leading to considerable interest in ethylene oxide derivatives. Ironically, this commercial movement from ethylene oxide to ethanolamines recapitulated the history of the synthesis of the chemicals as Wurtz's synthesis of ethanolamines in 1860 was largely the result of his trying to figure out what he could make with a new chemical he had discovered just the year before—ethylene oxide.

In the post-war years, significant process improvements were subsequently made as a result of the burgeoning interest in ethanolamines, which had proven to be extremely versatile intermediates in a wide variety of chemical products such as emulsifiers, surfactants, and agrichemicals, as well as many others. Examples of such improvement can be seen in, for example, U.S. Pat. No. 2,196,554 to Guinot which discloses an aqueous process with an improved heat integration and efficiency scheme for the concentration of ethanolamines in the process backend. Another example is GB Patent No. 760, 215 to Lowe et al., which discloses that by controlling the molar ratios at which ammonia and ethylene oxide are mixed, then a higher content of di- or tri-ethanolamine may be obtained. Alternatively, GB Patent No. 1 529 193 to Gleich discloses that a higher di- or tri-ethanolamine content may be obtained by recycling di- or tri-ethanolamine to the reactor.

Given that the conversion of reactants to products is nearly complete in an ethanolamines process and the fact that the process has developed into a mature technology by process improvements such as those mentioned above, wringing out additional improvements or competitive technical advantages in ethanolamines technology has proved difficult. Opportunities for process improvement in ethanolamines reside mainly in product quality and thermal and utility efficiency. For example, reducing the amount of water used in the process would significantly improve the utility efficiency and process economics, since this means less water must be removed later in the process. Water content can only be reduced, without negatively affecting product quality, by maintaining lower temperatures. Product quality is related to temperature because higher temperatures in an ethanolamines process often lead to discoloration of the ethanolamines product. Thus, there has been a considerable effort to reduce the ratio of water to ammonia used in the process.

However, attempts to achieve an economically desirable ratio of water to ammonia have proved largely unsuccessful as doing this often leads to excess pressures in the bottom of the absorber (since as the ratio of water to ammonia in a solution decreases, the vapor pressure in the solution increases). If the absorber backpressures the rest of the recycle and recovery sections this can require that the temperatures in the bottom of the stripping column and evaporator columns be increased, which can in turn result in a loss of product quality. For example, U.S. Pat. No. 4,119,670 notes that the high temperatures required for ammonia stripping often results in a discolored alkanolamines product. U.S. Pat. No. 4,335,181 discloses a process for decreasing the water to ammonia ratio, but expresses concern that in doing so the temperature in the bottom of the stripping column should be no greater than 150° C.

Accordingly, there is a continuing need in the art for an ethanolamine manufacturing process with the improved process economics and efficiency of operating at high ammonia to water ratios and that also produces quality, on-spec product.

BRIEF SUMMARY OF THE INVENTION

The present invention relates to a process for the preparation of ethanolamines comprising the steps of: (a) mixing a recycle water ammonia solution comprising from about 45% to about 60% ammonia and about 40% to about 55% water with ethylene oxide to form a reactor inlet composition; (b) charging the reactor inlet composition to one or more amine reactors; (c) reacting the ammonia with the ethylene oxide in the one or more amine reactors to form an effluent reaction mixture comprising unreacted ammonia, water and ethanolamines; (d) separating, in a first ammonia stripping column, the effluent reaction mixture into a rich ammonia-water mixture vapor overhead and a product solution bottoms liquid, the water-ammonia mixture vapor overhead comprising a first portion of the unreacted ammonia, and the product solution comprising a remaining portion of the unreacted ammonia, and the ethanolamines; (e) separating, in a second ammonia stripping column, the product solution into a second stripping column vapor overhead comprising the remaining portion of the unreacted ammonia, and a water-ethanolamines solution; (f) preparing a lean ammonia-water mixture in the second absorber from the second stripping column vapor overhead; (g) mixing the lean ammonia-water mixture with the water-ammonia mixture vapor overhead in a first absorber to prepare the recycle water ammonia solution; (h) separating, in a first evaporator, the water-ethanolamines solution into steam overhead and a concentrated water-ethanolamines solution; and (i) further concentrating the concentrated water-amines solution, in a second evaporator.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 is a schematic flow sheet for a process for preparing ethanolamines according to the present invention.

DETAILED DESCRIPTION OF THE INVENTION

All parts, percentages and ratios used herein are expressed by volume unless otherwise specified. All documents cited herein are incorporated by reference.

By "water" it is meant any kind of water suitable for use in chemical and petrochemical processing, including deionized, demineralized, industrial, potable and distilled water.

An improved ethanolamines process has been discovered in the present invention where the economic and thermal efficiency benefits of using a high ammonia to water ratio are combined with the production of a high quality ethanolamines product. The heat integration of the process is designed in such a way as to reduce the operating temperatures throughout the breadth of the process. In particular, temperatures are maintained below 150° C. almost everywhere in the process of the present invention.

The process of the present invention will now be described in detail with specific reference to FIG. 1. A reactor inlet composition is prepared by combining a source of ethylene oxide with a water-ammonia solution. Preferably, this water-ammonia solution is a water-ammonia solution that is prepared in the first absorber 27 (described below) and supplied through conduit 50. The water-ammonia solution comprises from about 45% to about 60% ammonia and about 40% to about 55% water. The reactor inlet composition contains ammonia and ethylene oxide at a molar ratio of about 2:1 to about 40:1 ammonia:ethylene oxide.

The reactor inlet composition is fed to the one or more amine reactors (a single reactor 17 is shown in FIG. 1). Either adiabatic, isothermal or a combination of both reactors may be used in the process. Preferably a series of tubular reactors are used. The one or more reactors are operated at a temperature and pressure to prevent vaporization of any of the components in the reactor inlet composition and ensure single-phase liquid operation. Accordingly, the temperature in the reactors should be maintained between 40° C. and 75° C. and the pressure between 1 MPa and 2 MPa. The ethylene oxide mixes with excess ammonia in the amine reactor so that the conversion of the ethylene oxide is nearly complete. The effluent reaction mixture from the one or more reactors is composed of ethanolamines (mono-, di-, and tri-) as well as unreacted ammonia and water. This effluent reaction mixture flows by pressure differential through conduit 18 to arrive at the first ammonia stripping column 21 (hence the pressure in the first stripping column must be maintained less than that in the one or more reactors 17—preferably the pressure in the first stripping column 21 is from about 0.45 MPa to about 0.65 MPa).

In the first stripping column 21, a first portion of the unreacted ammonia is separated from the effluent reaction mixture. As the effluent reaction mixture moves downward in the column, separation by steam-stripping of the effluent reaction mixture takes place with the upwardly-moving steam (provided by a steam source) contacting the effluent reaction mixture and separating the more volatile components, especially ammonia, from the mixture. However, only a first portion of the unreacted ammonia, this first portion comprising about 60% to 90% of the unreacted ammonia, is separated from the effluent reactor mixture. The aforementioned first portion passes as vapor to the overhead; a remaining portion of the unreacted ammonia remains in the effluent reactor mixture and moves downward into the bottoms liquids.

Thus, a rich ammonia-water mixture vapor overhead is formed comprising the first portion of the unreacted ammonia, water vapor and optionally other components in the vapor phase. The vapor-phase first stripping column overhead flows through conduit 24 by pressure differential to the first absorber 27 (and so by definition the first absorber 27 is operated at a pressure that is less than the pressure of the first ammonia stripper 21). Specifically, the first absorber 27 is operated at a pressure of about 0.4 MPa to about 0.6 MPa.

Also as a result of the aforementioned separation a product solution is formed in the bottom of the first stripping column 21 comprising the remaining portion of the ammonia, the ethanolamines, and other less volatile components of the effluent reaction mixture. This product solution is taken from the first stripping column 21 as a liquid bottoms stream and through conduit 30 to the second ammonia stripping column 33.

A substantial advantage of the present invention can be seen in the operation of the first stripping column 21 in that because it is not necessary to strip or separate all of the unreacted ammonia from the reaction mixture, relatively low temperatures may be used in the first stripping column 21: for example the bottoms temperature in the first ammonia stripping column 21 is operated in the range of about 80° C. to about 100° C. while the overhead temperature is maintained in the range of about 60° C. to about 85° C.

In the second ammonia stripping column 33, the remaining portion of the unreacted ammonia is separated. The product solution from the first ammonia column 21 flows through conduit 30 and enters the top portion of the second ammonia stripping column 33 and as the product solution moves downward in the column, separation by steam-stripping of the product solution takes places with upwardly-moving steam contacting the product solution and separating the ammonia and other more volatile components from the product solution. The steam is provided to the second ammonia stripping column 33 through conduit 57 from the overhead vapors of the first evaporator 53 (discussed below). Thus, a second stripping column overhead comprising the remaining portion of the unreacted ammonia, water vapor, and optionally one or more of the more volatile components of the product solution is formed in gaseous phase. Additionally, in the bottom of the second stripping column 33 an ethanolamines-water solution is formed comprising the less volatile components of the product solution especially water and the ethanolamines product as well as other components besides water and ethanolamines. The second ammonia stripping column 33 is operated at a pressure of about 0.15 MPa to about 0.25 MPa, while the bottoms temperature of the second stripping column 33 is about 120° C. to about 130° C. and the overhead temperature is between about 70° C. and about 85° C.

The second stripping column overhead flows by pressure differential through conduit 36 to the second absorber 43 for the remaining portion of the ammonia to be recovered for recycle back to the reactors (and thus the second absorber 43 is operated at a pressure that is less than the pressure of the second ammonia stripper 33). Specifically, the second absorber 43 is operated at a pressure of about 0.1 MPa to about 0.3 MPa. A lean ammonia-water mixture comprising about 25% to about 35% ammonia and 65% to 75% water is prepared in the second ammonia absorber 43 from the second stripping column overhead and, optionally, additional amounts of water. This lean ammonia-water mixture is taken through the bottoms stream from the second absorber 43 and pumped through conduit 47 to the first ammonia absorber 27. The first absorber 27 receives this lean ammonia-water mixture and mixing it with the first striping column overhead received through conduit 24 makes a recycle water-ammonia solution comprising about 45% to about 60% ammonia and 40% to 55% water. An ammonia-water solution is prepared in the first ammonia absorber 27 by a liquid ammonia make-up stream (not shown) in order to replace the ammonia used in the reaction and maintain the ammonia concentration in the recycle water-ammonia solution at the levels disclosed above. This water-ammonia solution is then supplied through conduit 50 to the reactor 17.

The ethanolamines-water solution is taken as a bottoms stream from the second stripping column 33 and moved through conduit 39 to the middle portion of the first evaporator 53.

In the first evaporator 53, the ethanolamines-water solution moves downward in the column and separation occurs by steam-stripping of the ethanolamines-water solution to reduce the water content and produce a concentrated water-ethanolamines product solution in the bottom of the evaporator. The bottoms temperature of the first evaporator 53 is between about 145° C. to about 155° C. (this is the maximum temperature of the present invention—and the maximum temperature experience by the aqueous ethanolamines) and the overhead temperature is between about 135° C. to about 145° C. The overhead vapor (steam) from the first evaporator 53 is supplied through conduit 57 to provide a heat and vapor source to the second stripping column 33. The concentrated water-amines product solution prepared flows through the bottom of the first evaporator 53 and through conduit 60 into the second evaporator 63. The second evaporator 63 is operated at a bottoms temperature of about 110° C. to about 120° C. and an overhead temperature of about 90° C. to about 110° C. In the second evaporator 63 the concentrated amines product-water solution is further concentrated and is sent from the bottoms stream through conduit 67 to a drying column (not shown) to reduce the water content even further, then to refining and separation steps (not shown). The overhead vapor (steam) from the second evaporator 63 may be used as a vapor and heat source for the drying column (not shown).

The first 21 and second 33 stripping columns, the first 27 and second 43 absorbers and the first evaporator 53 and second evaporator 63 are constructed so as to facilitate intimate vapor-liquid contact and any suitable arrangement or configuration that accomplishes this is acceptable. The columns' internals may be selected from either multiple-tray configurations or random or structured packing. The first 21 and second 33 stripping columns may be combined and configured as a single column with an internal head dividing the first and second stripping sections each comprised of multi-tray internals. Similarly, the first 27 and second 43 absorbers may be combined into a single column with an internal head dividing the first absorber from the second absorber and each containing random or structured packing.

Ethylene Oxide Production

Ethylene oxide is produced by continuously contacting an oxygen-containing gas with an olefin, preferably ethylene, in the presence of an ethylene oxide ("epoxidation") catalyst (described in greater detail below). Oxygen may be supplied to the reaction in substantially pure molecular form or in a mixture such as air. By way of example, typical reactant feed mixtures under operating conditions may contain from about 0.5% to about 45%, preferably about 5% to about 43% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process. Both have adverse effects on the catalyst, so the concentrations of these components are usually kept at a minimum.

Also present in the reaction, as previously mentioned, are one or more chloride moderators. Non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

A usual method for the ethylene epoxidation process comprises the vapor-phase oxidation of ethylene with molecular oxygen, in the presence of an epoxidation catalyst (to be defined in greater detail herein below), in a fixed-bed tubular reactor. Conventional, commercial fixed-bed ethylene-oxide reactors are typically in the form of a plurality of parallel elongated tubes (in a suitable shell) approximately 20 to 70 mm O.D. and 15 to 65 mm I.D. and 5-16 meters long filled with catalyst. Such reactors include a reactor outlet which allows the olefin oxide, un-used reactants, and byproducts to exit the reactor chamber.

The ethylene oxide that is reacted with ammonia in the present invention may be supplied from OSBL or may be supplied by an ethylene oxide process that is integrated with the ethanolamines process in the same chemical complex.

Epoxidation Catalyst

The epoxidation catalyst that can be used in the present invention includes a silver-based epoxidation catalyst that has a selectivity of greater than 83 mole %. The silver-based epoxidation catalyst that can be used in the present invention includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. In one embodiment of the present application, the epoxidation catalyst that can be used is a silver-based, rhenium-containing epoxidation catalyst which may also include one or more additional promoters. The support employed in this invention may be selected from a large number of solid, refractory supports that may be porous and may provide the preferred pore structure. Alumina is well known to be useful as a catalyst support for the epoxidation of an olefin and is the preferred support.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. Equivalent diameter is the diameter of a sphere having the same external surface (i.e., neglecting surface within the pores of the particle) to volume ratio as the support particles being employed.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used.

In some embodiments of the present invention, a promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and, if present, rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), optional rhenium component, and optional additional promoter(s) will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include operability (resistance to runaway), selectivity, activity, conversion, stability and yield, among other catalytic properties. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various promoters can be employed.

After impregnation of the support with the silver-containing compound, i.e., a silver precursor, optional promoters such as, for example, rhenium and/or alkali metals, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

For purposes of illustration only, the following are conditions that are often used in current commercial ethylene oxide reactor units: a gas hourly space velocity (GHSV) of 1500-10,000 $h^{-1}$, a reactor inlet pressure of 1 Mpa to 3 MPa, a coolant temperature of 180-315° C., an oxygen conversion level of 10-60%, and an EO production rate (work rate) of 100-350 kg EO/$m^3$ catalyst/hr and a change in ethylene oxide concentration, $\Delta EO$, of from about 1.5% to about 4.5%. The feed composition in the reactor inlet after the completion of start-up and during normal operation typically comprises (by volume %) 1-40% ethylene, 3-12% $O_2$; 0.2% to 10%, preferably 0.2% to 6%, more preferably 0.2% to 5% of $CO_2$; 0-5% ethane, an amount of one or more chloride moderators, which are described herein; and the balance of the feed being comprised of argon, methane, nitrogen or mixtures thereof.

We claim:

1. A process for the preparation of ethanolamines comprising the steps of:
    (a) mixing a water-ammonia solution comprising from about 45% to about 60% ammonia and about 40% to about 55% water with ethylene oxide to form a reactor inlet composition;
    (b) charging the reactor inlet composition to one or more amine reactors;
    (c) reacting the ammonia with the ethylene oxide in the one or more amine reactors to form an effluent reaction mixture comprising unreacted ammonia, water and ethanolamines;
    (d) separating, in a first ammonia stripping column, the effluent reaction mixture into a rich ammonia-water mixture vapor overhead and a product solution bottoms liquid, the water-ammonia mixture vapor overhead comprising a first portion of the unreacted ammonia, and the product solution bottoms liquid comprising a remaining portion of the unreacted ammonia, and the ethanolamines;
    (e) separating, in a second ammonia stripping column, the product solution bottoms liquid into a second stripping column vapor overhead comprising the remaining portion of the unreacted ammonia, and a water-ethanolamines solution;
    (f) preparing a lean ammonia-water mixture in a second absorber from the second stripping column vapor overhead;
    (g) mixing the lean ammonia-water mixture with the water-ammonia mixture vapor overhead in a first absorber to prepare the water-ammonia solution;
    (h) separating, in a first evaporator, the water-ethanolamines solution into steam overhead and a concentrated water-ethanolamines solution; and
    (i) further concentrating the concentrated water-ethanolamines solution, in a second evaporator.

2. The process according to claim 1, where the ammonia and ethylene oxide are present in a ratio of ammonia:ethylene oxide of about 2:1 to about 40:1.

3. The process according to claim 1, further comprising the step of passing the steam overhead from the first evaporator to the second stripping column by pressure differential to provide the second stripping column with a source of vapor and heat.

4. The process according to claim 1, wherein a maximum temperature of the ethanolamines is from about 145° C. to about 155° C.

5. The process according to claim 1, further comprising the step of passing the rich ammonia-water mixture vapor overhead from the first ammonia stripping column by pressure differential to the first absorber.

6. The process according to claim 5, wherein the pressure in the first ammonia stripping column is between about 0.45 MPa to about 0.65 MPa.

7. The process according to claim 1, wherein the bottoms temperature in the first ammonia stripping column is operated in the range of about 80° C. to 100° C. while the overhead temperature is maintained in the range of about 60° C. to about 85° C.

8. The process according to claim 1, wherein the ethylene oxide is manufactured by contacting an oxygen-containing gas with ethylene in the presence of an epoxidation catalyst.

9. The process according to claim 8, wherein the epoxidation catalyst is a silver-based epoxidation catalyst that includes at least a promoting amount of rhenium.

10. The process according to claim 1, wherein the first portion of the unreacted ammonia comprises about 60% to about 90% of the unreacted ammonia.

11. The process according to claim 1, wherein the lean ammonia-water mixture comprises from about 25% to about 35% ammonia and about 65% to about 75% water.

* * * * *